(12) United States Patent
Wabel et al.

(10) Patent No.: US 12,144,914 B2
(45) Date of Patent: Nov. 19, 2024

(54) APPARATUS CONTAINING A DIALYSIS SOLUTION

(71) Applicant: Fresenius Medical Care Deutschland GmbH, Bad Homburg (DE)

(72) Inventors: Peter Wabel, Rosbach (DE); Robert Berlich, St. Wendel (DE); Marcus Breuninger, Bad Homburg (DE); Birgit Staude, Pfungstadt (DE); Matthias Rau, Wiesbaden (DE); Stefan Weiss, Bad Homburg (DE); Zdenek Cerman, Idstein (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 942 days.

(21) Appl. No.: 16/971,356

(22) PCT Filed: Feb. 14, 2019

(86) PCT No.: PCT/EP2019/053676
§ 371 (c)(1),
(2) Date: Aug. 20, 2020

(87) PCT Pub. No.: WO2019/162185
PCT Pub. Date: Aug. 29, 2019

(65) Prior Publication Data
US 2020/0390955 A1    Dec. 17, 2020

(30) Foreign Application Priority Data

Feb. 21, 2018   (DE) .................... 102018103866.6

(51) Int. Cl.
*A61M 1/16*      (2006.01)
*A61M 39/10*     (2006.01)

(52) U.S. Cl.
CPC .......... *A61M 1/1668* (2014.02); *A61M 39/10* (2013.01)

(58) Field of Classification Search
CPC ...... B65D 81/20; B65D 77/06; B65D 77/042; B65D 25/289; B65D 5/606; A61M 1/1668; A61M 39/10; A61M 2209/082
USPC ......................................... 206/438
See application file for complete search history.

(56) References Cited

U.S. PATENT DOCUMENTS

| 4,326,526 | A |   | 4/1982 | Buck et al. |
| 4,397,643 | A | * | 8/1983 | Rygiel ................. A61M 1/602 |
|           |   |   |        | 600/573 |
| 4,573,992 | A | * | 3/1986 | Marx ..................... A61M 1/02 |
|           |   |   |        | 604/408 |

(Continued)

FOREIGN PATENT DOCUMENTS

| DE | 19825568 | 12/1999 |
| DE | 10319874 | 8/2004 |

(Continued)

OTHER PUBLICATIONS

Japanese Office Action.

*Primary Examiner* — Ernesto A Grano
(74) *Attorney, Agent, or Firm* — Jacobson Holman PLLC

(57) ABSTRACT

The present invention relates to an apparatus for transporting a dialysis solution, wherein the apparatus has a flexible inner bag for receiving the dialysis solution that is arranged in a rigid outer packaging that is preferably parallelepiped-shaped.

14 Claims, 4 Drawing Sheets

(56) References Cited

U.S. PATENT DOCUMENTS

Figure 1:
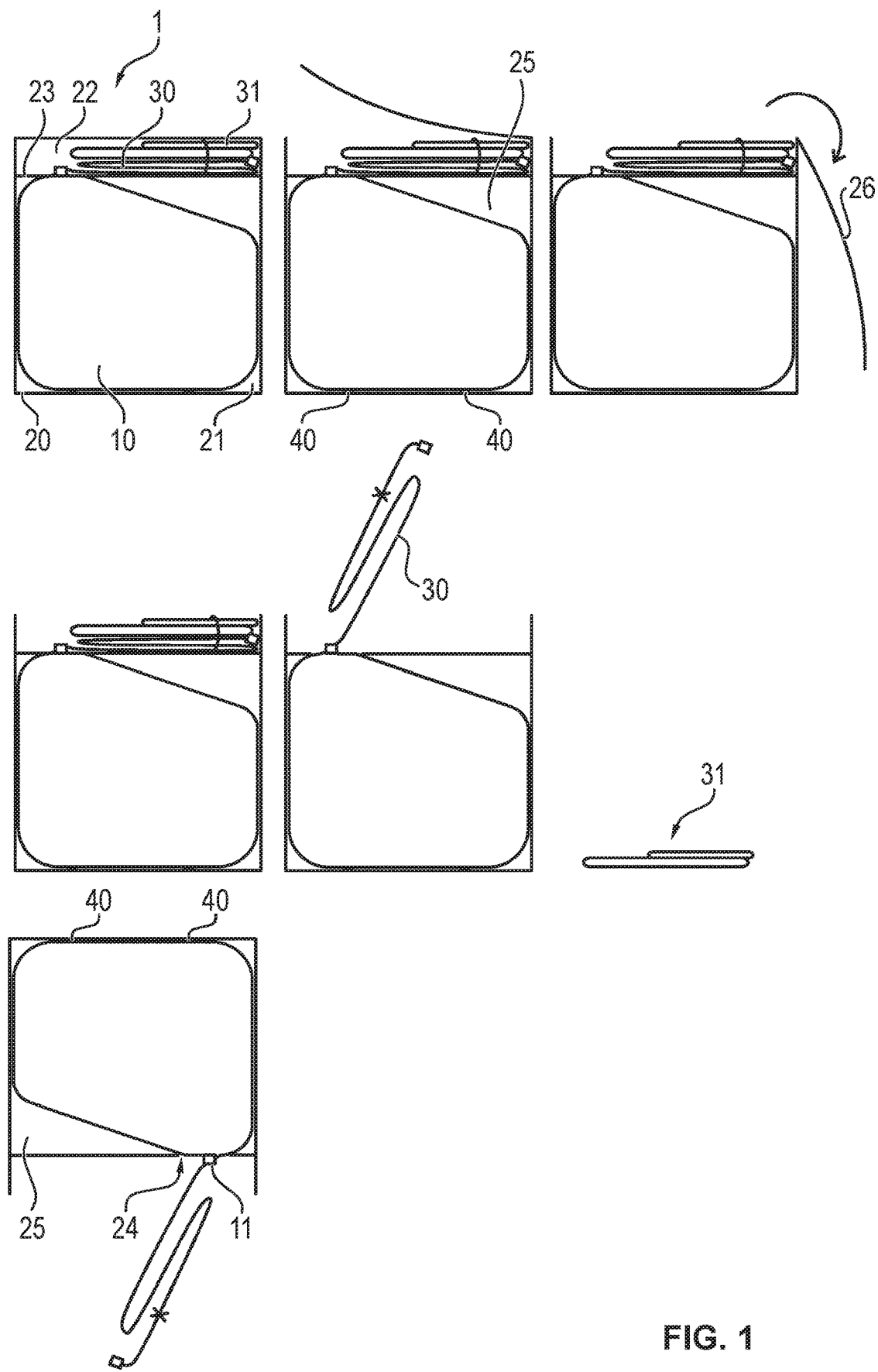

| | | | | |
|---|---|---|---|---|
| 4,629,080 | A * | 12/1986 | Carveth | B29C 66/8322 |
| | | | | 215/11.4 |
| 4,771,917 | A * | 9/1988 | Heaps, Jr. | B65D 77/061 |
| | | | | 222/105 |
| 4,869,398 | A | 9/1989 | Colvin et al. | |
| 5,211,643 | A * | 5/1993 | Reinhardt | A61M 1/287 |
| | | | | 604/416 |
| 5,390,814 | A * | 2/1995 | Christine | A61J 1/05 |
| | | | | 222/105 |
| 5,399,166 | A | 3/1995 | Laing | |
| 5,425,447 | A * | 6/1995 | Farina | A61J 1/2093 |
| | | | | 383/88 |
| 5,858,015 | A * | 1/1999 | Fini | A61J 1/10 |
| | | | | 422/44 |
| 6,012,578 | A * | 1/2000 | Keilman | A61M 1/28 |
| | | | | 604/408 |
| 6,641,562 | B1 * | 11/2003 | Peterson | A61M 5/14244 |
| | | | | 604/141 |
| 6,682,517 | B1 * | 1/2004 | Ezaki | B29C 66/71 |
| | | | | 604/408 |
| 7,104,978 | B2 * | 9/2006 | Hilgers | A61M 1/1656 |
| | | | | 604/408 |
| 8,080,301 | B2 * | 12/2011 | Goodwin | A61B 50/30 |
| | | | | 150/156 |
| 8,262,602 | B2 * | 9/2012 | Lee | A61M 1/28 |
| | | | | 604/179 |
| 8,986,253 | B2 * | 3/2015 | DiPerna | A61M 5/1486 |
| | | | | 604/141 |
| 9,132,220 | B2 * | 9/2015 | Kugelmann | A61J 1/2093 |
| 10,039,992 | B2 * | 8/2018 | Rivera | A61J 1/03 |
| 10,201,475 | B2 * | 2/2019 | Jöbstl | B65D 77/04 |
| 10,500,032 | B2 * | 12/2019 | Risch | B65D 81/268 |
| 10,537,098 | B2 * | 1/2020 | Matsumura | A01N 1/0268 |
| 10,589,197 | B2 * | 3/2020 | Rhodes | C12M 33/14 |
| 2008/0093246 | A1 * | 4/2008 | Duchamp | B65D 5/307 |
| | | | | 210/646 |
| 2008/0208159 | A1 * | 8/2008 | Stanus | A61J 1/1475 |
| | | | | 604/408 |
| 2012/0292215 | A1 * | 11/2012 | Bertoni | A61M 39/20 |
| | | | | 206/438 |
| 2013/0015204 | A1 * | 1/2013 | Gol | A61P 3/00 |
| | | | | 222/541.6 |
| 2015/0290080 | A1 * | 10/2015 | Weikart | A61J 1/062 |
| | | | | 206/438 |

FOREIGN PATENT DOCUMENTS

| | | |
|---|---|---|
| JP | 11-513915 | 11/1999 |
| JP | 57-55150 | 7/2015 |
| WO | WO97/45149 | 12/1997 |

* cited by examiner

APPARATUS CONTAINING A DIALYSIS SOLUTION

The invention relates to an apparatus for transporting a dialysis solution contained therein.

It is in particular customary in the field of peritoneal dialysis to provide the patient with solution bags that are filled with a dialysis solution suitable for the patient. The patient then connects these solution bags to an inflow hose, i.e. to the patient catheter, independently or with the aid of trained medical personnel to fill the peritoneum with the solution. The dialysis solution typically has to be transported to the patient's home in the fully prepared state.

It is the object of the invention to provide an apparatus for transporting a dialysis solution with which a safe transport can be ensured with costs and waste production that are as small as possible.

Against this background, the invention relates to an apparatus containing a dialysis solution and to a medical connector for connecting the apparatus to a line that leads to a patient and that has a flexible inner bag for receiving the dialysis solution that is arranged in a rigid outer packaging. On the use of the apparatus, a dialysis solution is received within the inner bag. The outer packaging is preferably a parallelepiped-shaped box.

Such a bag-in-box packaging has the advantage that the inner bag, that is typically formed as a disposable element, is protected from mechanical influences by the outer packaging. The mechanical robustness of the solution bag, here an inner bag, has reduced importance with respect to previously known solutions, whereby a material-saving and less expensive design is made possible. The cost saving and the saving of waste are in particular considerable due to the fact that the solution bags are typically disposable products. The outer packaging can be designed as more complex and optionally also with additional functions such as reservoirs or patient-specific labels. The manufacturing costs and the material effort play a lesser role here due to the possibility of multiple use. On the other hand, the outer packaging can, for example, be manufactured from cardboard in a cost-saving and environmentally friendly manner. The outer packaging can be designed such that a stacking of the apparatus can be optimized.

The inner bag is typically produced from plastic films that are connected to one another along weld seams. Since dialysis solutions often contain a bicarbonate buffer, multilayer films having low gas permeability are preferably used.

The preferably parallelepiped-shaped outer packaging can be produced from a rigid plastic material, from metal, or from cardboard.

Provision is made in an embodiment that the inner bag is fastened to at least one, and preferably to a plurality of inner walls of the outer packaging, with provision preferably being made that fastening elements that can be reversibly connected to one another are provided at the inner wall or walls and at the bag. The position of the bag in the outer packaging can be defined and stabilized by such a fastening. Examples include mechanical connections such as latch connections, plug-in elements having projections at the bag, and corresponding apertures or guides at the outer packaging as well as corresponding hooks and receivers. In addition to the reversibly releasable fastenings, fastenings can be considered that cannot be released in a nondestructive manner such as an adhesive bonding or welding.

Provision is made in an embodiment that the inner bag has at least one extraction port for the extraction of dialysis solution that comprises the medical connector, with provision preferably being made that the outer packaging has an extraction opening or an extraction perforation, with the extraction port and the extraction opening or extraction perforation being arranged relative to one another such that access can be made to the extraction port through the extraction opening or extraction perforation. The inner bag can, for example, be arranged in and fastened to the outer packaging such that the extraction port is arranged directly behind or in the extraction opening or extraction perforation. The inner bag and the outer packaging can also be connected to one another in the region of the extraction port or extraction perforation to fix the position of the extraction port relative to the extraction opening or extraction perforation. The extraction opening itself can, for example, be closed by a removable film or flip-cover to keep the extraction port sterile. Alternatively or additionally, the port can be closed, preferably in a sterile manner, by a removable cap or by a removable covering.

Provision is made in an embodiment that the inner bag is arranged in the outer packaging such that the extraction port is arranged in at least one possible standing position of the outer packaging at the lowest point of the bag. It can thus be ensured that liquid can flow off completely from the inner bag. For example, a ramp that extends obliquely to the respective side surface can be arranged at at least one side surface in the parallelepiped-shaped outer packaging. The bag can thus lie at a slant on the ramp. The extraction port can be arranged at the end of the ramp close to the side surface. Alternatively, the bag can be shaped such that one side of the bag, that is disposed opposite a side of the bag fastened to the inner side of the outer packaging, is sloped. The extraction port can be arranged at the end of the slope.

Provision is made in an embodiment that the outer packaging has a suspension apparatus at a corner or side edge and that the inner bag is arranged in the outer packaging such that the extraction port contacts the oppositely disposed corner or side edge of the outer packaging. If the outer packaging is suspended at a suitable stand using the suspension apparatus, the extraction port is then at the lowest point so that liquid can flow off completely out of the inner bag.

Provision is made in an embodiment that the inner bag has at least one filling port for its filling with dialysis solution, with provision preferably being made that the outer packaging has a filling opening, with the filling port and the filling opening being arranged relative to one another such that access can be made to the filling port through the filling opening. A filling of the bag already located in the outer packaging is thus made possible. The inner bag can, for example, be arranged in and fastened to the outer packaging such that the filling port is arranged directly behind or in the filling opening or extraction perforation. The inner bag and the outer packaging can also be connected to one another in the region of the filling port and the filling opening to fix the position of the filling port relative to the filling opening. Such a fixing is preferably realized by a latch connection, a weld connection, or an adhesive connection.

In an embodiment, the inner bag has at least two ports, a filling port for its fitting with dialysis solution and an extraction port for extracting dialysis solution. The filling port can be arranged at a side of the apparatus disposed opposite the extraction port.

Provision is made in an embodiment that the outer packaging comprises at least two compartments, with the inner bag being arranged in one of the two compartments. The other compartment is free and can be used for accommodating tube sets or other accessory parts such as gloves or the like. The bag compartment is preferably dimensioned such that it is substantially filled by the filled bag.

Provision can be made in an alternative variant that the inner bag completely fills up the outer packaging. Tube sets and accessory parts can, for example, be arranged in a film packaging at the outside of the outer packaging.

Provision is made in an embodiment that the outer packaging has a cover that releases an opening in the inner space of the outer packaging. The cover can, for example, be arranged such that access can be made to a compartment of the inner space in which the bag is not arranged, but in which a tube set and/or accessory parts is/are arranged. The cover can, for example, be formed by a section of the outer packaging separated by perforation lines. The outer packaging can be designed such that the inner space is terminated in a sterile manner with respect to the environment before an opening of the cover.

Provision is made in an embodiment that the apparatus has a gripping element for carrying the apparatus, with provision preferably being made that the gripping element is fastened to the inner bag and passes to the outside through a gripping opening in the outer packaging. The force is directly introduced into the inner bag by such an arrangement, with the inner bag typically being heavier than the outer packaging due to its filling with dialysis solution.

Provision is made in an embodiment that the outer packaging is designed such that it can be collapsed in a defined manner by folding along predefined axes. The box can, for example, have defined fold lines or side surfaces having a plurality of surfaces foldable with respect to one another. Pressure can be exerted onto the inner bag by a collapsing from outside the outer packaging to facilitate the former's complete emptying. A collapsed container is furthermore easier to transport and has a smaller waste volume in the event of disposal.

Provision is made in an embodiment that the outer packaging has an inspection window to be able to monitor the filling level of the inner bag. This can be of advantage, for example, when the apparatus is used as a drain bag for consumed dialysis solution after the emptying of the inner bag. The inspection window can, for example, be provided with filling level marks.

Provision is made in an embodiment that the outer packaging is designed as gas-tight. An additional gas barrier can thereby be provided, which increases the service life of the bicarbonate-buffered dialysis solutions, on the one hand, and enables a design of the inner bag that has thinner walls and is thus more cost-saving and material-saving.

Provision is made in an embodiment that the container is produced from sterilizable materials. The materials are preferably of such a nature that they are of stable shape at temperatures that are customary within the framework of a heat sterilization of a dialysis solution, that is, for example, at approximately 120° C., and do not decompose or emit pollutants.

Provision is made in an embodiment that all the inner spaces of the container that are closed with respect to the environment and that contain medical liquids or ports are sterile. This in particular applies to the inner volume of the inner bag and to the medical connector.

Figure 3:
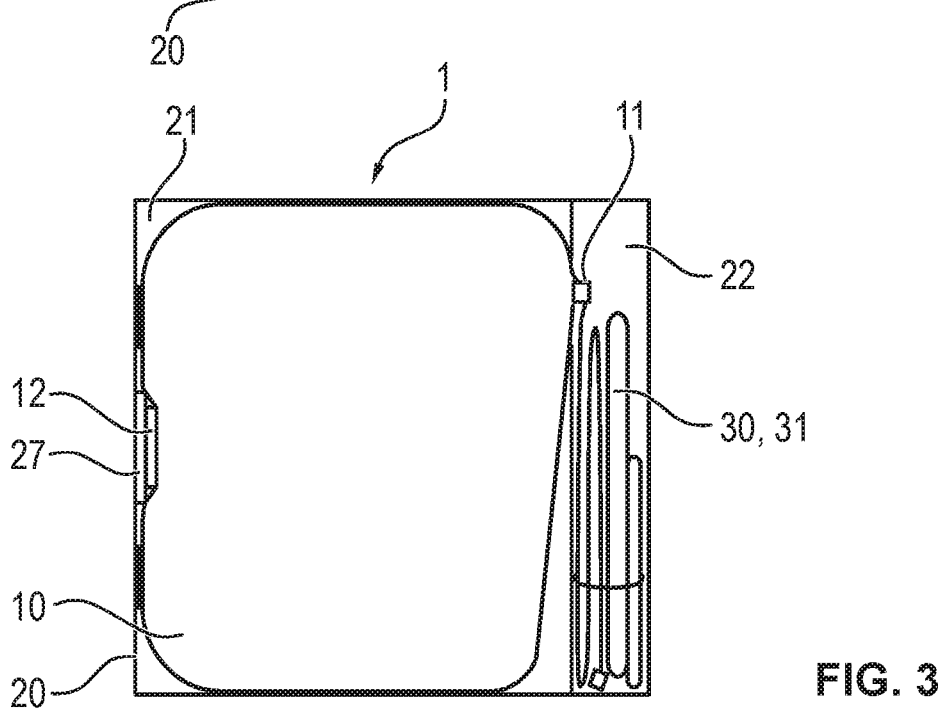
Figure 4:
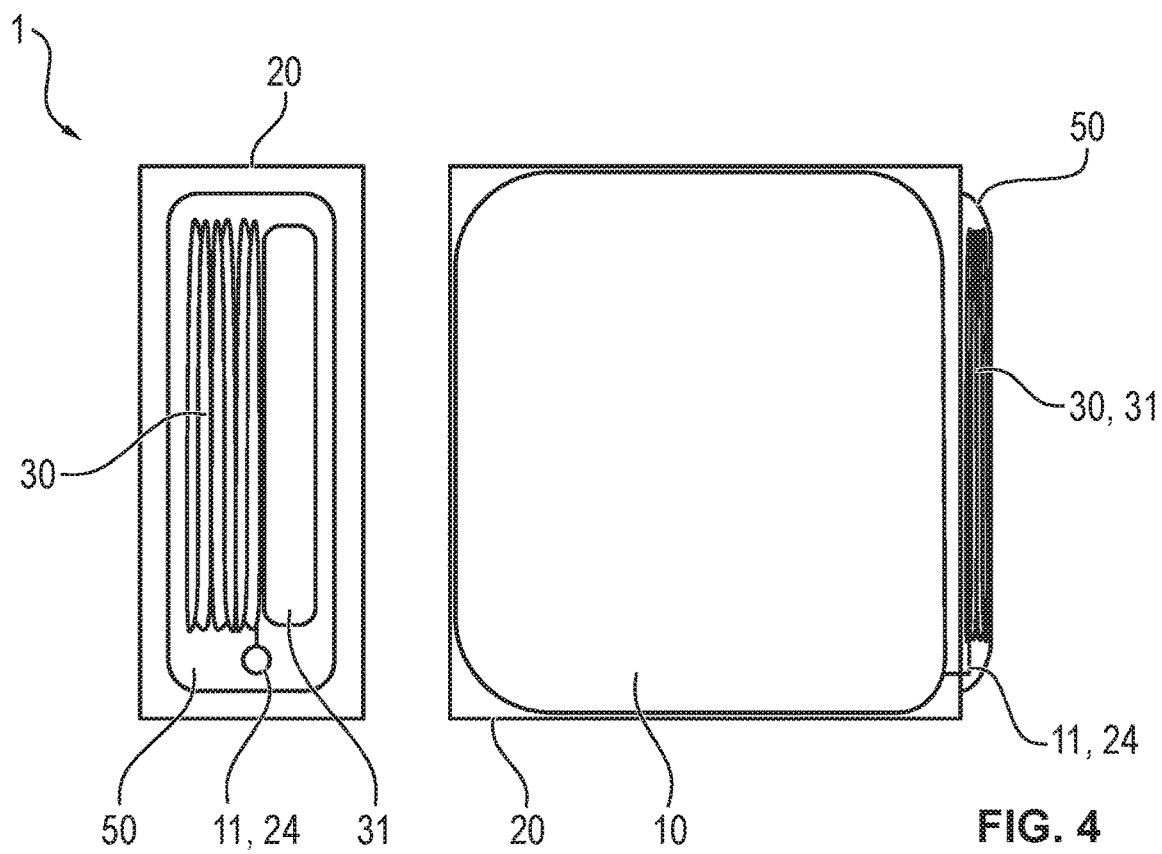
Figure 5:
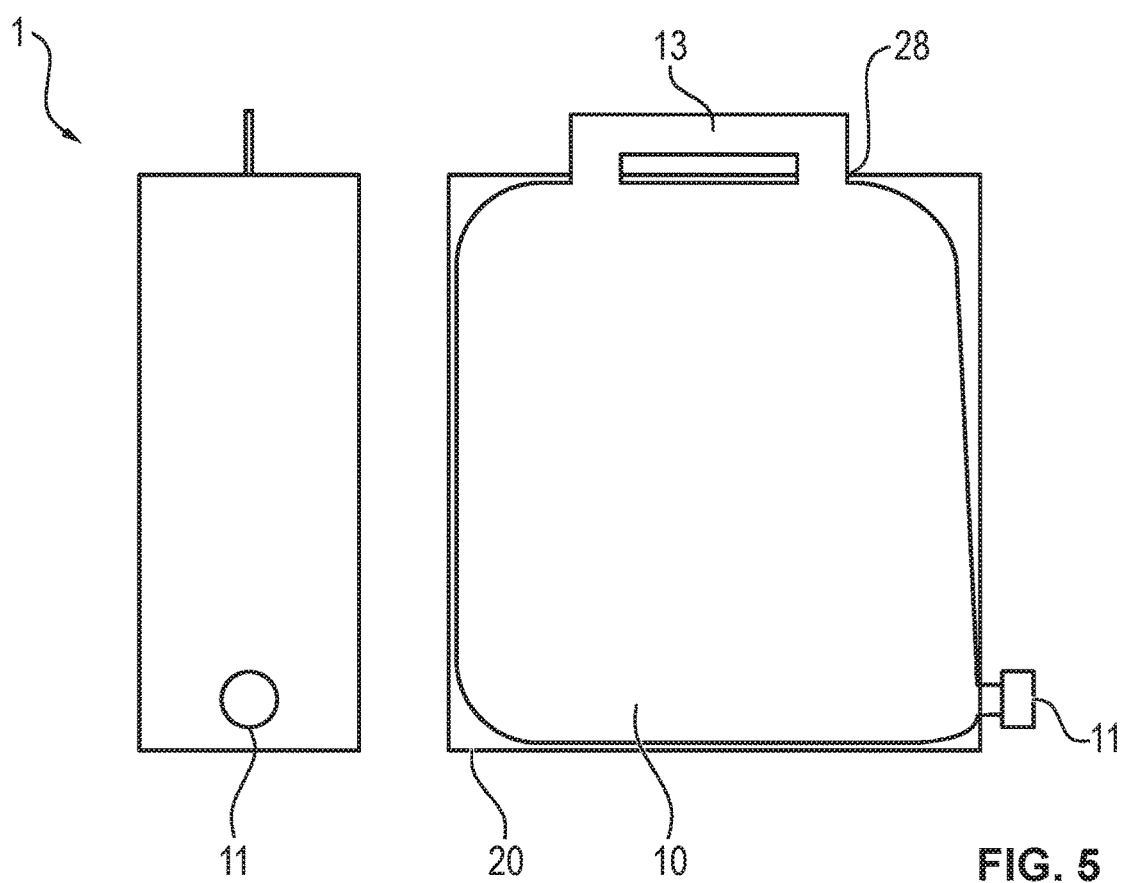
Figure 6A:
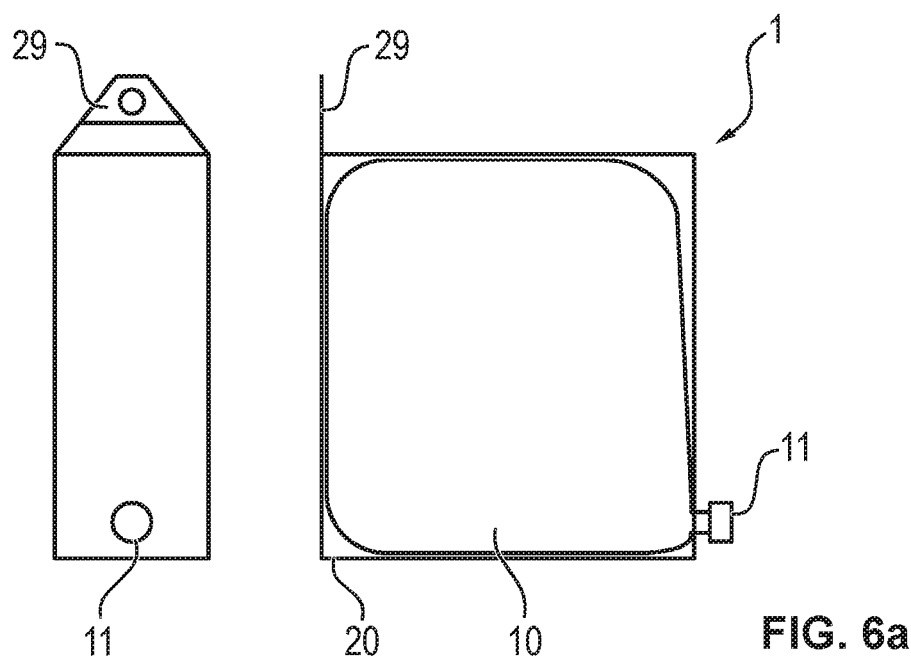
Figure 6B:
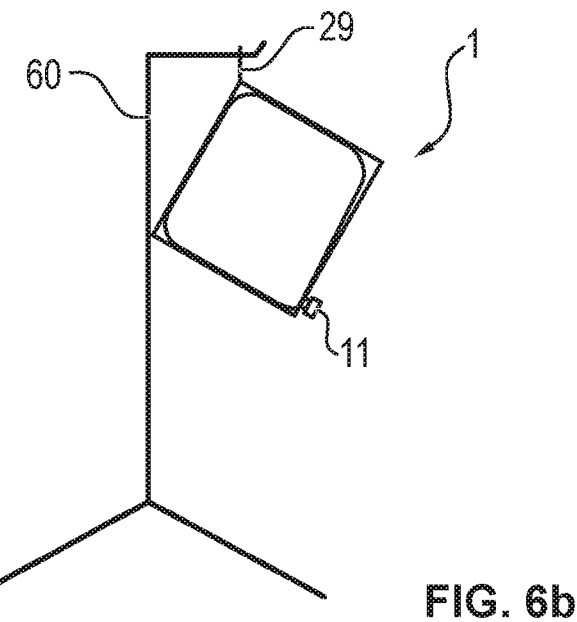
Figure 7:
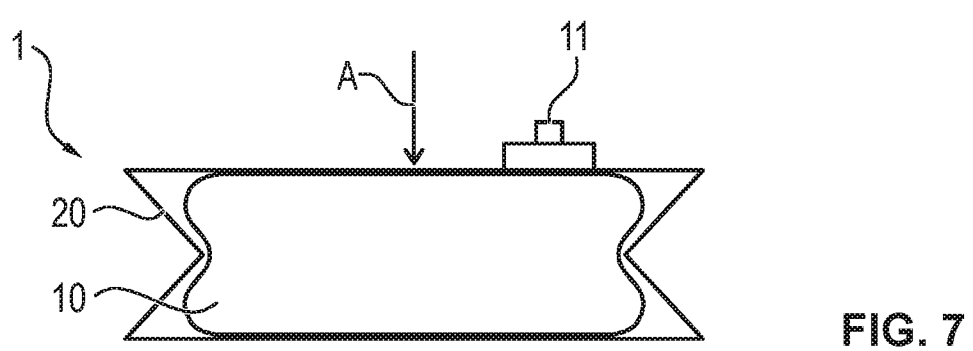

Further details and advantages of the invention result from the embodiments described in the following with reference to the Figures. There are shown in the Figures:

FIG. 1: a first embodiment of a transport box in accordance with the invention in different stages of use;

FIG. 2: possibilities for fastening the solution bag to the outer packaging;

FIG. 3: further representations of the box in accordance with FIG. 1;

FIG. 4: an alternative variant of the transport box in accordance with the invention;

FIG. 5: a possible further development of the transport box in accordance with FIG. 4;

FIG. 6: a further possible development of the transport box in accordance with FIG. 4; and FIG. 7: a collapsible variant of a box in accordance with the invention.

An embodiment of a transport box in accordance with the invention is shown in FIG. 1. The transport box 1 represents a double packaging in the manner of a bag-in-box packaging for dialysis solutions. It comprises an inner bag 10 that is mechanically supported and protected by a rigid outer packaging 20. The box 1 is intended to be filled with ready-to-use dialysis solution in a treatment center or in an automatic output machine, that is optionally mobile, and then to be transported home by the patient.

The box 1 is shown in the state in which it is handed over to the patient in the top left image. The box 1 will now first be described in this state.

Both the parallelepiped-shaped outer packaging 20 and the inner bag 10 are designed as disposable products, with the outer packaging comprising cardboard and being able to be recycled in an environmentally friendly manner and being able to be manufactured very inexpensively. The inner bag 10 is produced from multi-layer plastic films that are connected to one another along weld seams. The mechanical robustness of the inner bag 10, however, loses importance with respect to already known solutions, whereby a material-saving and less expensive design of the inner bag 10 is made possible.

The outer packaging 20 comprises two compartments 21 and 22 that are separated by an intermediate wall 23, with the inner bag 10 being arranged in a large bag compartment 21. A tube set 30 is accommodated in the small tube compartment 22 and is combined with further accessory parts 31 such s gloves and the like to form a bundle. The bag compartment 21 and the inner bag 10 are dimensioned such that the inner bag 10 substantially completely fills up the bag compartment 21, i.e. except for a ramp-like cut-out 25. The ramp-like cut-out 25 in the bag compartment 21 is a consequence of a special shape of the inner bag 10 and of a fastening of the inner bag 10 to the inner walls of the bag compartment 21 in the embodiment shown. As an alternative, the arrangement of a ramp belonging to the outer packaging 20 within the bag compartment is also conceivable. The function of the ramp-like cut-out 25 will be described further below.

The inner bag 10 has an extraction port 11 for the extraction of dialysis solution. The extraction port 11 of the inner bag 10 reaches through an extraction opening 24 in the intermediate wall 23 into the tube compartment 22 and is preconnected to the tube set 30 so that the patient no longer has to connect the tube set 30 to the extraction port 11 on a following use. Although this cannot be recognized in any more detail in FIG. 1, the inner bag 10 and the outer packaging 20 are connected to one another in the region of the extraction port 11 and of the extraction opening 24 to fix the position of the extraction port 11 in the extraction opening 24.

The inner bag 10 is also fastened to a plurality of points at the wall of the bag compartment 21 disposed opposite the intermediate wall 23. The corresponding fastening points are marked by reference numeral 40.

Figure 2A:
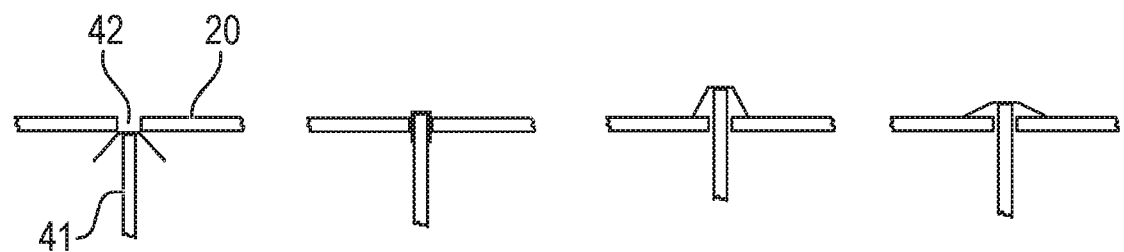

The fastenings can, for example, be configured as adhesive dots or as welds. A releasable embodiment is furthermore conceivable in which the solution bag 10 is provided with barbs 41 and the wall of the outer packaging 20 is provided with reception holes 42 such as is shown in FIG. 2a.

Figure 2B:
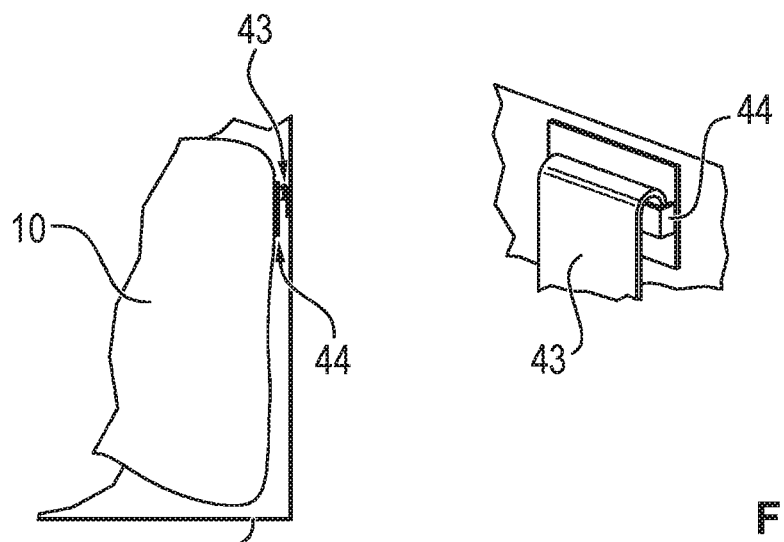

The inner bag can also be fastened to the walls of the outer packaging 20 at the side in FIG. 1 in an embodiment to stabilize its position within the outer packaging. A fastening by means of adhesive spots or welds or a releasable fastening is in turn conceivable, for example in the manner as shown in FIG. 2b, with corresponding holding projections 43 and 44 at the solution bag 10 and the outer packaging 20.

The outer packaging 20 has a cover 26 that bounds the tube compartment 22 at its side disposed opposite the intermediate wall 23. The cover 26 extends over the entire corresponding side of the outer packaging 20 and comprises, like the remaining parts of the outer packaging 20, cardboard, with it being separated from the remaining parts of the outer packaging 20 by a perforation line.

The course of the use of the box 1 at the patient's is schematically explained in the further images of FIG. 1.

The standing box 1 of the top left image is first opened by tearing the cover 26 along the perforation line and by a subsequent folding open of the cover 26 so that the patient can access the upwardly disposed tube compartment 22. The tube set 30 connected to the extraction port 11 and the accessories 31 are then removed from the tube compartment 22. The box is then rotated by 180° so that the extraction port 11 is at the bottom. In this position, the box can, for example, be placed at an elevated position or can be fastened to a stand such that is in an elevated position with respect to the patient. A slipping of the inner bag 10 out of the outer packaging 20 is prevented in this position by the fastening to the fastening points 40. The extraction port is at the lowest point due to the special shape of the inner bag 10 that leaves the ramp-like cut-out 25 free and due to its fixing to the now upwardly disposed side of the bag compartment 21 so that the inner bag 10 can be completely emptied by gravity during the treatment.

FIG. 3 again shows the box 1 already described while looking at FIG. 1, with a further detail of the box being recognizable here, namely a filling port 12 at the side of the inner bag 10 disposed opposite the extraction port 11, i.e. at that side of the inner bag 10 that is fixed at the fastening points 40 to the inner wall of the bag compartment 21 of the outer packaging 20. The outer packaging 20 has a filling opening 27 at a point corresponding to the filling port 12 and the filling port 12 can be accessed through it from the outside so that a filling of the inner bag 10 already located in the outer packaging 20 is made possible.

The inner bag 10 therefore has exactly two ports, namely the filling port 11 for its filling with dialysis solution and the extraction port 12 for the extraction of dialysis solution. The filling port 11 is arranged at the side of the inner bag 10—or also of the outer packaging 20 and the box 1 as a whole—disposed opposite the extraction port 12.

An alternative variant of the box in accordance with the invention is shown in FIG. 4 in which the outer packaging 20 only has one compartment that is substantially completely filled by the inner bag 10. A tube compartment is missing in this variant. The tube set 30 and the accessories 31 are instead received in a film packaging 50 at the outside of the outer packaging 20. The extraction opening 24 of the outer packaging 20 is arranged below the film packaging and is covered by it in an air-tight manner. The extraction port 11 of the inner bag 10 reaches through this extraction opening 24 into the inner space of the film packaging 50 and is preconnected to the tube set 30 so that the patient now only has to open the film packaging on a subsequent use and no longer has to connect the tube set 30 to the extraction port 11.

A further variant of a box 1 in accordance with the invention is shown in FIG. 5, with a gripping element 13 for carrying the box 1 being fastened to the inner bag 10 and passing to the outside through a gripping opening 28 in the outer packaging 20. The force is directly introduced into the inner bag 10 by such an arrangement when carried, with the inner bag typically being heavier than the outer packaging 20 due to its filling with dialysis solution. The extraction port 11 is configured as in FIG. 4, with the film packaging 50 no longer being shown separately.

In the variant of a box 1 in accordance with the invention shown in FIG. 4, the wedge-shaped recess 25 in the inner space of the outer packaging 25 is missing in comparison with the variant shown in FIG. 1 so that when the box 1 is placed flat on its bottom, the inner bag 10 does not run toward its extraction port 11. The extraction port 11 and the corresponding extraction opening 24 are, however, arranged in the region of a side edge of the outer packaging 20 so that the inner bag is arranged at the lowest point of the inner bag on a slanted positioning of the box 1.

The box 12 can therefore, as is shown in FIG. 6a, have suspension tab 29 at the side edge of the outer packaging 20 disposed opposite the extraction port 11 and the extraction opening 24 and the box 1 can be suspended by said suspension tab, as shown in FIG. 6b, at an infusion stand 60, for example. In the suspended state, the extraction opening 11 is then, as can be recognized in FIG. 6b, automatically at the lowest point of the box, whereby a complete gravimetric emptying of the inner bag 10 is made possible.

A variant of the transport box 1 in accordance with the invention is shown in FIG. 7 in which the outer packaging 20 is designed such that it can be collapsed by a folding of the side walls along horizontal axes if pressure is exerted on the upper side of the box in the direction of the arrow A. A complete emptying of the inner bag 10 can be promoted by the exertion of pressure even if the inner bag 10 does not run toward the extraction opening 11.

The invention claimed is:

1. An apparatus containing a dialysis solution and a medical connector for connecting the apparatus to a line leading to the patient,
   characterized in that the apparatus comprises
   a sterile bag space and a sterile tube space,
   a flexible inner bag disposed in the sterile bag space for receiving the dialysis solution that is arranged in
   a rigid outer packaging having a top wall, a wall opposing the top wall, and side walls and an extraction opening in the wall opposing the top wall, and
   a tube set disposed in the sterile tube space for carrying the dialysis solution from the inner bag to the patient,
   wherein the outer packaging has a suspension apparatus at a corner or side edge between the top wall and one of the side walls, and the inner bag has an extraction port as the medical connector and is arranged in the outer packaging such that the extraction port extends through the extraction opening of the outer packaging and connects to the flexible tubing.

2. An apparatus in accordance with claim 1, characterized in that the inner bag is fastened to at least one inner wall of the outer packaging, the sterile bag and tube spaces are separate bag and tube compartments of the outer packaging, respectively, with the wall opposing the top wall being an intermediate wall separating the tube compartment from the bag compartment, and the outer packaging further has a cover, such that the top wall, side walls, and intermediate wall border the bag compartment and the intermediate wall, side walls, and cover border the tube compartment.

3. An apparatus in accordance with claim 2, characterized in that the extraction port protrudes through the extraction opening into the tube compartment.

4. An apparatus in accordance with claim 1, characterized in that the sterile bag space is the outer packaging, the outer packaging has as a bottom wall the wall that opposes the top wall having an extraction opening, and the sterile tube space is a film packaging covering outside the bottom wall including the extraction opening in an airtight manner.

5. An apparatus in accordance with claim 4, characterized in that the extraction port protrudes through the extraction opening into the tube space.

6. An apparatus in accordance with claim 4, characterized in that the apparatus has a gripping element for carrying the apparatus.

7. An apparatus in accordance with claim 4, characterized in that the outer packaging is configured such that it can be folded together in a defined manner by a folding along predefined axes.

8. An apparatus in accordance with claim 4, characterized in that the apparatus has a gripping element for carrying the apparatus, and in that the gripping element is fastened to the inner bag and passes to the outside through a gripping opening in the outer packaging.

9. An apparatus in accordance with claim 4, characterized in that the inner bag is arranged in the outer packaging such that the extraction port is arranged in at least one possible standing position of the outer packaging at the lowest point of the bag.

10. An apparatus in accordance with claim 1, characterized in that the inner bag has at least one filling port for its filling with dialysis solution.

11. An apparatus in accordance with claim 1, characterized in that the apparatus is produced from sterilizable materials.

12. An apparatus in accordance with claim 1, wherein the rigid outer packaging is parallelepiped-shaped.

13. An apparatus in accordance with claim 1, characterized in that the inner bag is fastened to at least one inner wall of the outer packaging, and in that corresponding fastening elements that can be reversibly connected to one another are provided at the at least one inner wall and at the bag.

14. An apparatus in accordance with claim 1, characterized in that the inner bag has at least one filling port for its filling with dialysis solution, and in that the outer packaging has a filling opening, with the filling port and the filling opening being arranged relative to one another such that access can be made to the filling port through the filling opening.

* * * * *